US012691254B2

(12) United States Patent
Miyata

(10) Patent No.: US 12,691,254 B2
(45) Date of Patent: Jul. 28, 2026

(54) STYLET AND CATHETER ASSEMBLY

(71) Applicant: TERUMO KABUSHIKI KAISHA, Tokyo (JP)

(72) Inventor: Masakazu Miyata, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 515 days.

(21) Appl. No.: 18/214,005

(22) Filed: Jun. 26, 2023

(65) Prior Publication Data

US 2023/0347108 A1 Nov. 2, 2023

Related U.S. Application Data

(63) Continuation of application No. PCT/JP2022/000180, filed on Jan. 6, 2022.

(30) Foreign Application Priority Data

Jan. 13, 2021 (JP) ................................. 2021-003399

(51) Int. Cl.
*A61M 25/01* (2006.01)
*A61M 25/00* (2006.01)
(52) U.S. Cl.
CPC .... *A61M 25/0102* (2013.01); *A61M 25/0028* (2013.01); *A61M 25/0043* (2013.01); *A61M 2025/0063* (2013.01)
(58) Field of Classification Search
CPC .............. A61M 25/01; A61M 25/0102; A61M 25/0043; A61M 25/0046; A61M 25/09;
(Continued)

(56) References Cited

U.S. PATENT DOCUMENTS

| 4,596,563 A | * | 6/1986 | Pande ............... | A61M 25/0045 |
| | | | | 604/524 |
| 5,078,702 A | | 1/1992 | Pomeranz | |

(Continued)

FOREIGN PATENT DOCUMENTS

| JP | H05253304 A | 10/1993 |
| JP | 2015019851 A | 2/2015 |
| JP | 2018050722 A | 4/2018 |

OTHER PUBLICATIONS

EESR 22739321.2 / PCT/JP2022000180, Jun. 21, 2024.
International Search Opinion, PCT/JP2022/000180, Mar. 15, 2022.
International Search Report, PCT/JP2022/000180, Mar. 15, 2022.

*Primary Examiner* — Laura A Bouchelle
(74) *Attorney, Agent, or Firm* — MacMillan, Sobanski & Todd, LLC

(57) ABSTRACT

A stylet for axially stretching a catheter ensures flexibility in the distal side and a desired degree of stiffness in the proximal side to enable preferable insertion of a catheter assembly along a guidewire while preventing a kink or breakage. The stylet 50 includes a hollow outer layer tube 51 extending in an axial direction and a hollow inner layer tube 52 disposed in the inner periphery of the outer layer tube. The inner layer tube is formed from a material stiffer than that of the outer layer tube. In the inner layer tube, a distal portion has the inner periphery provided with a tapered diameter portion 52B having a diameter reduced toward the proximal side in the axial direction.

12 Claims, 13 Drawing Sheets

(58) Field of Classification Search
CPC .. A61M 2025/0063; A61M 2025/0901; A61B
1/00078
See application file for complete search history.

(56) References Cited

U.S. PATENT DOCUMENTS

| | | | | |
|---|---|---|---|---|
| 5,531,719 | A * | 7/1996 | Takahashi ......... | A61M 25/0045 |
| | | | | 604/525 |
| 6,626,859 | B2 | 9/2003 | von Segesser | |
| 8,579,805 | B2 * | 11/2013 | Accisano, III ...... | A61M 25/001 |
| | | | | 600/184 |
| 2010/0063480 | A1 | 3/2010 | Shireman | |
| 2010/0286657 | A1 | 11/2010 | Heck | |

* cited by examiner

STYLET AND CATHETER ASSEMBLY

CROSS REFERENCE TO RELATED APPLICATIONS

This application is a continuation of PCT Application No. PCT/JP2022/000180, filed Jan. 6, 2022, based on and claiming priority to Japanese Application No. JP2021-003399, filed Jan. 13, 2021, both of which are incorporated herein by reference in their entirety.

BACKGROUND OF THE INVENTION

The present invention relates to a stylet and a catheter assembly.

In the related art, percutaneous cardiopulmonary support (PCPS) has been provided for cardiopulmonary resuscitation, circulatory support, and respiratory support in emergency treatment. PCPS is a method for temporarily assisting and substituting cardiopulmonary function using an extracorporeal circulation device.

An extracorporeal circulation device includes an extracorporeal circulation circuit provided with, for example, a centrifugal pump, an oxygenator, a blood removal channel, and a blood supply channel and is configured to exchange gases in blood removed and supply the blood to the blood supply channel.

The blood removal channel and the blood supply channel in such an extracorporeal circulation circuit may employ, for example, a high-performance cannula disclosed in U.S. Pat. No. 6,626,859. The high-performance cannula (catheter assembly) disclosed in U.S. Pat. No. 6,626,859 is inserted into a living body with a mandrel (stylet) being inserted into a cannula body (catheter).

In this stylet, the distal side is required to be flexible so as not to damage a blood vessel when the catheter assembly is percutaneously inserted into a living body while the proximal side closer to the hand is required to ensure a predetermined degree of stiffness from an operability perspective.

On a related note, for example, a catheter disclosed in U.S. Pat. No. 5,078,702 is obtained by joining plastic materials having different qualities and different degrees of stiffness, thereby ensuring flexibility in the distal side and stiffness in the proximal side.

In a case where the catheter disclosed in U.S. Pat. No. 5,078,702 is employed as a stylet, since the catheter is obtained by joining plastic materials with different qualities, the materials with different qualities are not necessarily joined in a preferred manner depending on the compatibility between the materials, and overuse may result in a kink or breakage in a joint part.

To ensure flexibility in the distal side and a desired degree of stiffness in the proximal side while preventing a joint part from kinking or breaking, an inner layer tube may be disposed in the inner periphery of an outer layer tube at a position closer to the proximal side than a distal end of the outer layer tube by a predetermined length. However, when a stylet having this configuration is inserted into a living body along a guidewire while being inserted into a tube, the guidewire touches a step caused by the wall thickness of an inner layer tube, which may impede preferable insertion of a catheter assembly.

SUMMARY OF THE INVENTION

The invention has been made in light of the problem, and an object of the invention is to provide a stylet that ensures flexibility in the distal side and a desired degree of stiffness in the proximal side and enables preferable insertion of a catheter assembly along a guidewire while preventing a kink or breakage and to provide a catheter assembly.

Solution to Problem

A stylet that achieves the object is configured to be insertable into a catheter including a lumen that allows passage of blood. The stylet includes an outer layer tube extending in an axial direction and an inner layer tube disposed in the inner periphery of the outer layer tube, having a hollow shape, and formed from a material stiffer than that of the outer layer tube. In the inner layer tube, a distal portion has the inner periphery provided with a reduced diameter portion having a diameter reduced toward the proximal side in the axial direction.

A catheter assembly that achieves the object includes the above stylet and a catheter configured to allow insertion of the stylet.

Advantageous Effects of Invention

The above stylet and catheter assembly includes the outer layer tube extending in the axial direction and the inner layer tube disposed in the inner periphery of the outer layer tube and formed from a material stiffer than that of the outer layer tube. Accordingly, it is possible to ensure flexibility in the distal side and a desired degree of stiffness in the proximal side while preventing a kink or breakage. In addition, since the inner layer tube has the reduced diameter portion, when the catheter assembly is inserted into a living body along a guidewire, it is possible to pass the guidewire through the lumen of the inner layer tube along the reduced diameter portion without encountering a step in the wall thickness. Therefore, there are provided a stylet that ensures flexibility in the distal side and a desired degree of stiffness in the proximal side and enables preferable insertion of a catheter assembly along a guidewire while preventing a kink or breakage and a catheter assembly.

BRIEF DESCRIPTION OF THE DRAWINGS

FIG. 2 is a side view illustrating a catheter before a stylet according to the embodiment is inserted thereinto.

FIG. 11 is a side view illustrating a double lumen catheter before the stylet according to the embodiment is inserted thereinto.

DETAILED DESCRIPTION OF PREFERRED EMBODIMENTS

Hereinafter, embodiments of the present invention will be described with reference to the accompanying drawings. Note that the following description does not limit the technical scope or the significance of each term disclosed in the claims. Furthermore, dimensional ratios of the drawings are exaggerated for illustration purpose and may differ from actual ratios.

Figure 1:
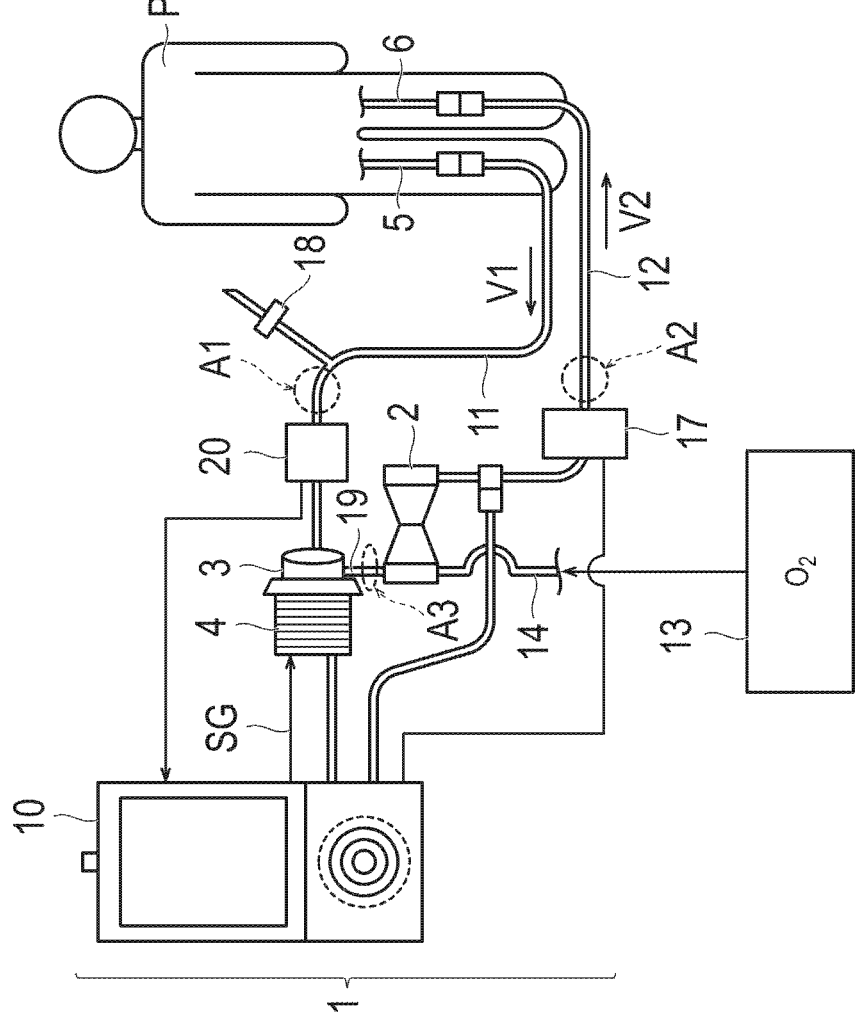
FIG. 1 is a system diagram illustrating an example of an extracorporeal circulation device employing a percutaneous catheter according to an embodiment of the invention.

FIG. 1 is a system diagram illustrating an example of an extracorporeal circulation device employing a percutaneous catheter according to an embodiment of the invention. The extracorporeal circulation device is used for percutaneous cardiopulmonary support (PCPS) in order to temporarily assist and substitute cardiopulmonary function of a patient with a weakened heart until recovery of heart function.

According to an extracorporeal circulation device 1, it is possible to perform surgery using a Veno-Arterial (VA) oxygenator. In this surgery, a pump is actuated to remove blood from a vein (vena cava) of a patient, and the oxygenator exchanges gases in the blood to oxygenate the blood, thereby returning the blood to an artery (aorta) of the patient. This extracorporeal circulation device 1 is used for assisting the heart and lungs. Hereinafter, a surgery to remove blood from a patient and perform predetermined treatment outside the body and return the blood into the patient's body will be referred to as "extracorporeal circulation".

As illustrated in FIG. 1, the extracorporeal circulation device 1 includes a circulation circuit for circulating blood. The circulation circuit includes an oxygenator 2, a centrifugal pump 3, a drive motor 4 as a drive unit for driving the centrifugal pump 3, a venous catheter (percutaneous catheter for blood removal) 5, an arterial catheter (catheter for blood supply) 6, and a controller 10 as a control unit.

The venous catheter (catheter for blood removal) 5 is inserted from the femoral vein, and through the inferior vena cava, a distal end of the venous catheter 5 is retained in the right atrium. The venous catheter 5 is connected to the centrifugal pump 3 through a blood removal tube (blood removal line) 11. The blood removal tube 11 is a channel for supplying blood.

The arterial catheter (catheter for blood supply) 6 is inserted from the femoral artery.

The drive motor 4 actuates the centrifugal pump 3 according to a command SG from the controller 10, causing the centrifugal pump 3 to remove blood from a patient P through the blood removal tube 11 and supply the blood to the oxygenator 2, and then, return the blood to the patient P through a blood supply tube (blood supply line) 12.

The oxygenator 2 is disposed between the centrifugal pump 3 and the blood supply tube 12. The oxygenator 2 exchanges gases in blood (oxygenates and/or decarbonates blood). The oxygenator 2 is, for example, a membrane oxygenator, and particularly preferably, a hollow fiber membrane brane oxygenator. To this oxygenator 2, an oxygen gas is supplied from an oxygen gas supply unit 13 through a tube 14. The blood supply tube 12 is a channel that connects the oxygenator 2 and the arterial catheter 6.

The blood removal tube 11 and the blood supply tube 12 may employ a channel made from, for example, a synthetic resin such as vinyl chloride resin and silicone rubber having high transparency and flexibility that enables elastic deformation. In the blood removal tube 11, blood, or a fluid, flows in V1 direction. In the blood supply tube 12, blood flows in V2 direction.

In the circulation circuit illustrated in FIG. 1, an ultrasonic bubble detection sensor 20 is disposed in a part of the blood removal tube 11. A fast clamp 17 is disposed in a part of the blood supply tube 12.

The ultrasonic bubble detection sensor 20 detects air bubbles mixed in the circulation circuit during the extracorporeal circulation which are caused by, for example, an erroneous operation of a three-way stopcock 18 or breakage of a tube. When the ultrasonic bubble detection sensor 20 detects air bubbles in blood being supplied to the blood removal tube 11, the ultrasonic bubble detection sensor 20 sends a detection signal to the controller 10. Based on this detection signal, the controller 10 issues an alarm and decreases the rotating speed of the centrifugal pump 3 or stops the centrifugal pump 3. Furthermore, the controller 10 commands the fast clamp 17 to immediately close the blood supply tube 12 by the fast clamp 17. This blocks air bubbles from being sent to the patient P's body. The controller 10 controls operations of the extracorporeal circulation device 1 to prevent air bubbles from entering the patient P's body.

The tube 11 (12 and 19) of the circulation circuit in the extracorporeal circulation device 1 is provided with a pressure sensor. The pressure sensor is attached to any one of or all of, for example, a fixing point A1 in the blood removal tube 11, a fixing point A2 in the blood supply tube 12 of the circulation circuit, and a fixing point A3 in the connecting tube 19 that connects the centrifugal pump 3 and the oxygenator 2. Accordingly, it is possible to measure pressure inside the tube 11 (12 and 19) by the pressure sensor during the extracorporeal circulation performed on the patient P by the extracorporeal circulation device 1. Note that the fixing point of the pressure sensor is not limited to the aforementioned fixing points A1, A2, and A3 and the pressure sensor may be attached to any points in the circulation circuit.

With reference to FIGS. 2 to 6, hereinafter described is a configuration of a percutaneous catheter (hereinafter referred to as "catheter") 30 into which a stylet 50 according to an embodiment of the invention is inserted. FIGS. 2 to 6 are views for describing the configuration of the catheter 30. This catheter 30 is used as the venous catheter (catheter for blood removal) 5 of FIG. 1. Note that the following configuration of the catheter 30 is an example and a catheter into which the stylet 50 according to this embodiment is inserted is not limited to the following configuration.

Figure 2:
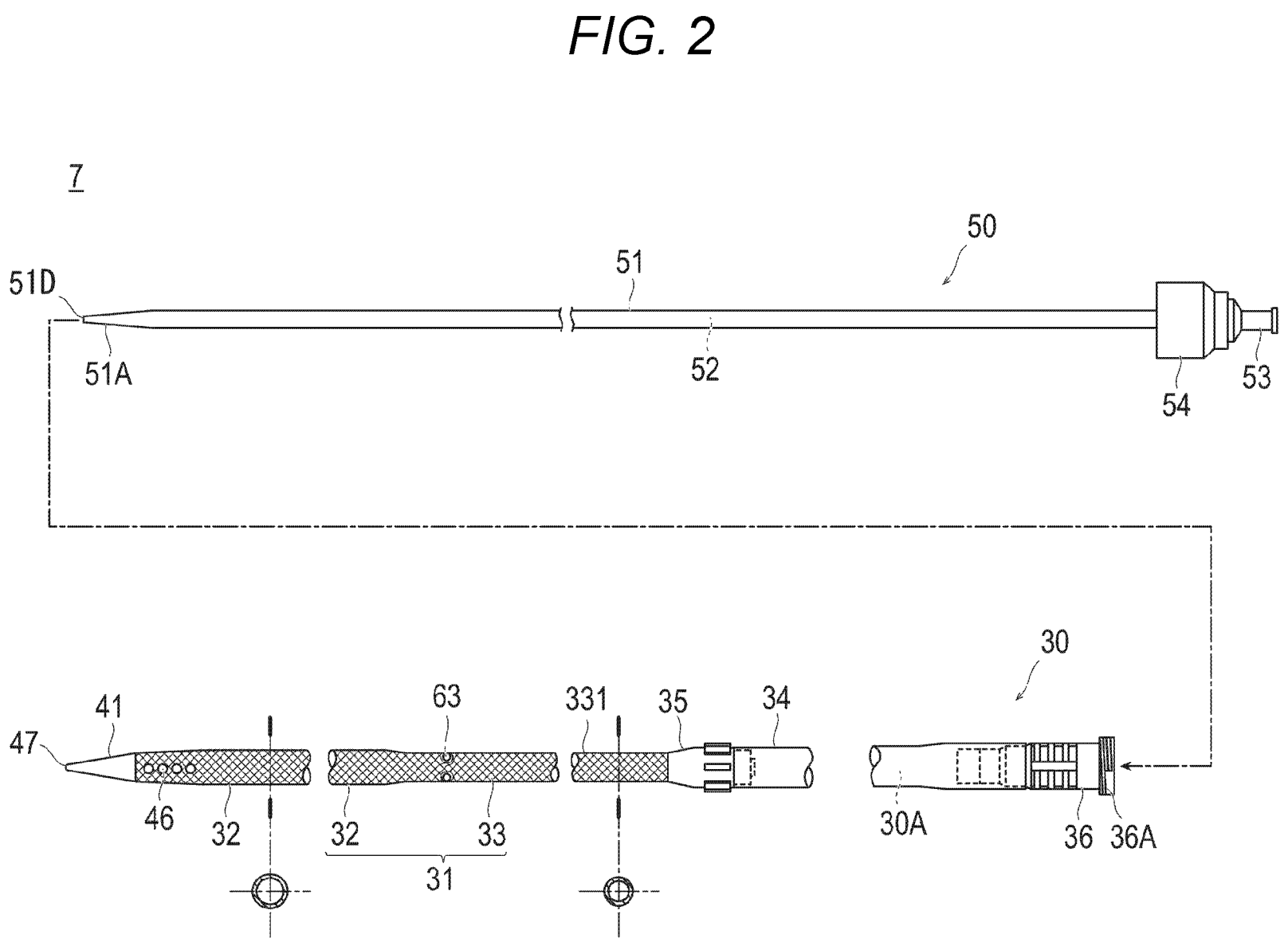

The catheter 30 includes, as illustrated in FIG. 2, a catheter tube 31 provided with a first side hole 63 and a second side hole 46, a distal tip 41 including a through-hole 47 and disposed on a distal end of the catheter tube 31, a clamping tube 34 disposed on the proximal side of the catheter tube 31, a catheter connector 35 for connecting the catheter tube 31 and the clamping tube 34, and a lock connector 36.

Herein, a side of the catheter 30 that is inserted into a living body is referred to as "distal end" or "distal side" and a side handled by an operator is referred to as "proximal end" or "proximal side". A distal portion represents a certain range including the distal end (the most distal part) and its periphery, while a proximal portion represents a certain range including the proximal end (the most proximal part) and its periphery.

Figure 3:
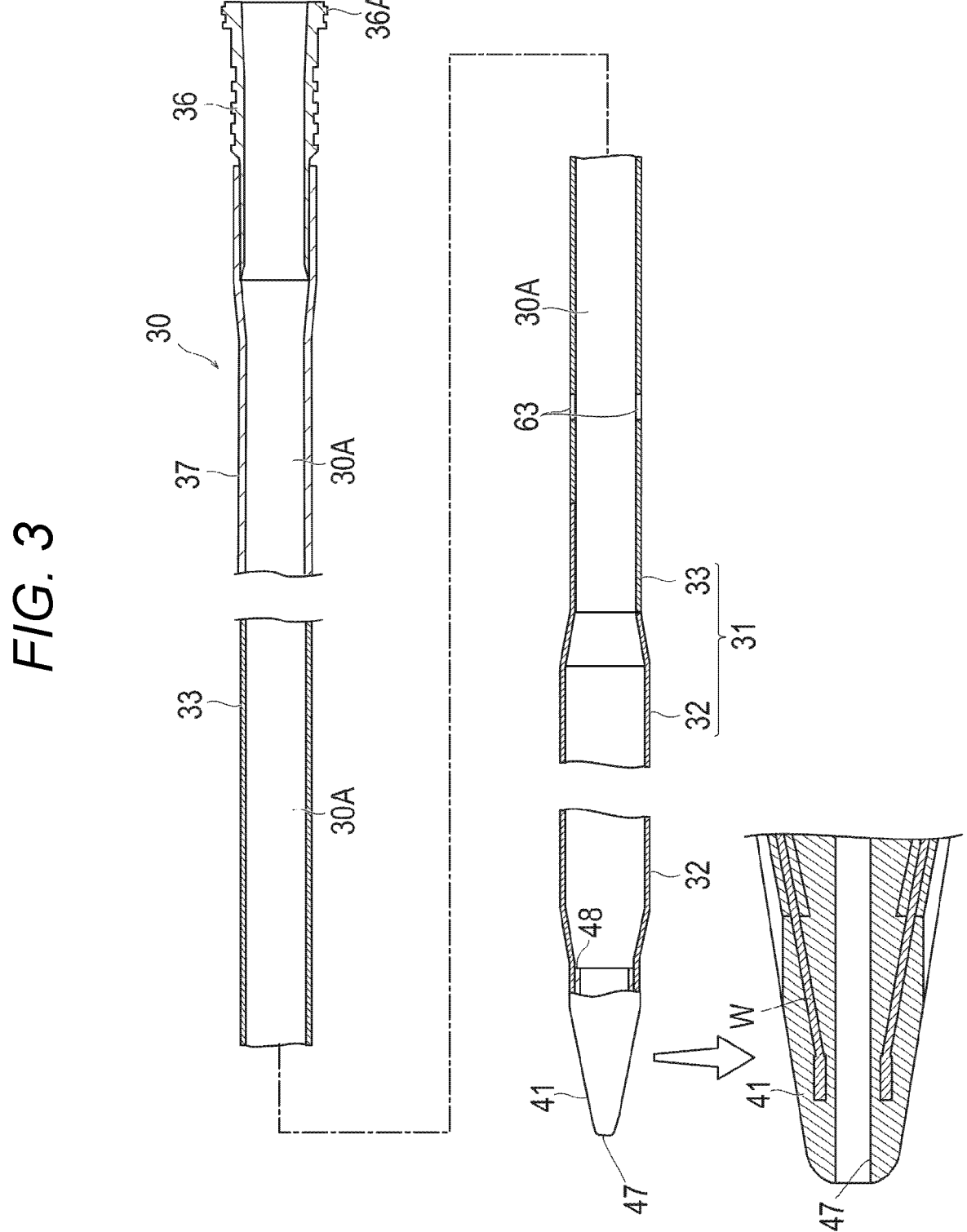
FIG. 3 is a cross-sectional side view of the catheter.

As illustrated in FIG. 3, the catheter 30 includes a lumen 30A penetrating the catheter 30 from a distal end to a proximal end. The through-hole 47 included in the distal tip 41 and the first side hole 63 and the second side hole 46 included in catheter tube 31 are placed in different objects of blood removal in a living body and are configured to remove blood efficiently.

When the catheter 30 is inserted into a living body, the stylet 50 as illustrated in FIG. 2 is used. The stylet 50 is inserted into the lumen 30A of the catheter 30 and combined with the catheter 30 in advance, and then, inserted into the living body. Herein, a combination of the catheter 30 and the stylet 50 is referred to as a catheter assembly 7.

Hereinafter described is each configuration of the catheter 30. Note that the catheter 30 is not limited to the following configurations.

The catheter tube 31 includes, as illustrated in FIG. 2, an enlarged portion 32 and a shaft portion 33 linked to the proximal side of the enlarged portion 32.

The enlarged portion 32 is configured to be higher in elasticity than the shaft portion 33. Furthermore, the enlarged portion 32 is configured to be larger than the shaft portion 33 in outside diameter and inside diameter.

The enlarged portion 32 and the shaft portion 33 have lengths long enough to place the through-hole 47 of the distal tip 41 and the first side hole 63 and the second side hole 46 of the catheter tube 31 in desired objects of blood removal. The enlarged portion 32 has a length of, for example, 20 to 40 cm and the shaft portion 33 has a length of, for example, 20 to 30 cm.

In this embodiment, the objects of blood removal are the right atrium and the inferior vena cava. The catheter 30 is inserted into a living body in such a manner that the through-hole 47 of the distal tip 41 and the second side hole 46 of the catheter tube 31 are placed in the right atrium while the first side hole 63 of the catheter tube 31 is placed in the inferior vena cava, whereby the catheter 30 is retained.

While the through-hole 47, second side hole 46, and first side hole 63 are placed in the objects of blood removal, the enlarged portion 32 is placed in the inferior vena cava, a relatively large blood vessel, and the shaft portion 33 is placed in the femoral vein, a relatively small blood vessel.

Figure 4:
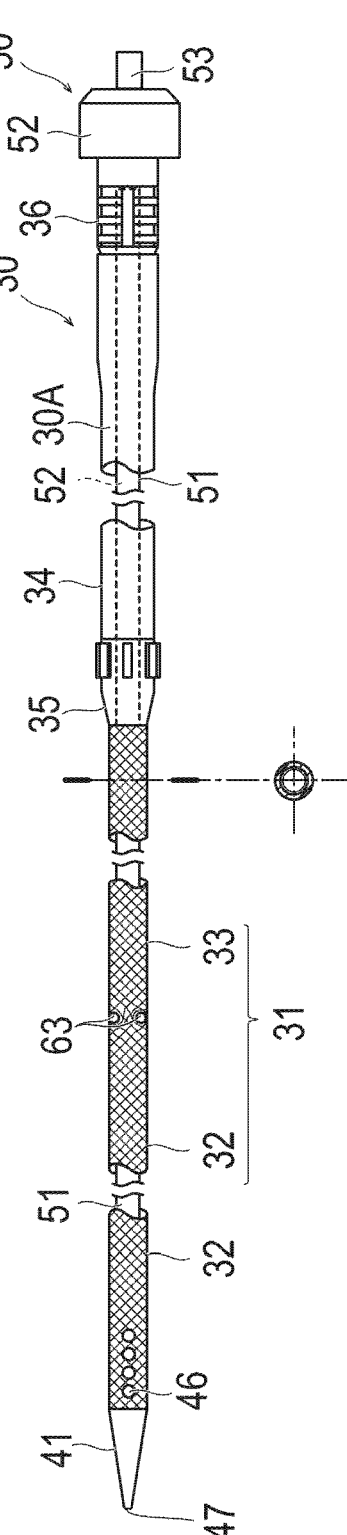
FIG. 4 is a side view illustrating the catheter after the stylet according to the embodiment is inserted thereinto.

When the stylet 50 is inserted into the lumen 30A of the catheter 30, the enlarged portion 32 having high elasticity extends in the axial direction and decreases in outside diameter and inside diameter as illustrated in FIG. 4. In this state, the outside diameter of the enlarged portion 32 becomes substantially equal to the outside diameter of the shaft portion 33. Since the catheter 30 is inserted into the living body while the enlarged portion 32 is extended in the axial direction and reduced in outside diameter and inside diameter, the catheter 30 is inserted in a minimally invasive manner.

After the catheter 30 is retained in the living body, the stylet 50 is retracted from the lumen 30A of the catheter 30, whereby the enlarged portion 32 extended in the axial direction shrinks and increases in inside diameter. At this time, the enlarged portion 32 is located in the inferior vena cava, a relatively large blood vessel. Accordingly, the enlarged portion 32 is increased in outside diameter, which is accompanied by an increase in inside diameter.

A pressure loss occurring for a blood flow inside the enlarged portion 32 is obtained by the following expression:

overall length of the enlarged portion 32×(average) channel cross-sectional area. In other words, an increase in inside diameter of the enlarged portion 32 reduces the pressure loss inside the enlarged portion 32. A reduction of the pressure loss inside the enlarged portion 32 increases an amount of blood flowing through the circulation circuit. For this reason, in order to obtain a sufficient amount of circulating blood, it is required to increase the inside diameter of the enlarged portion 32.

However, in a case where the wall thickness is made substantially constant, increasing the inside diameters of the enlarged portion 32 and the shaft portion 33 increases the outside diameters of these portions, which causes a heavy burden on a patient when inserting the catheter 30 into the living body and impedes the minimally invasive operation.

From the above perspectives, the enlarged portion 32 is designed to have an inside diameter of, for example, 9 to 11 mm and the shaft portion 33 is designed to have an inside diameter of, for example, 4 to 8 mm. Furthermore, the enlarged portion 32 and the shaft portion 33 are designed have a wall thickness of, for example, 0.4 to 0.5 mm.

In addition, as illustrated in FIG. 2, a distal portion of the enlarged portion 32 preferably has a portion gradually tapered toward the distal side in the axial direction from the center of the enlarged portion 32. Accordingly, the inside diameter of the distal end of the enlarged portion 32 becomes continuous with the inside diameter of the distal tip 41 disposed in the distal side.

Figure 5:
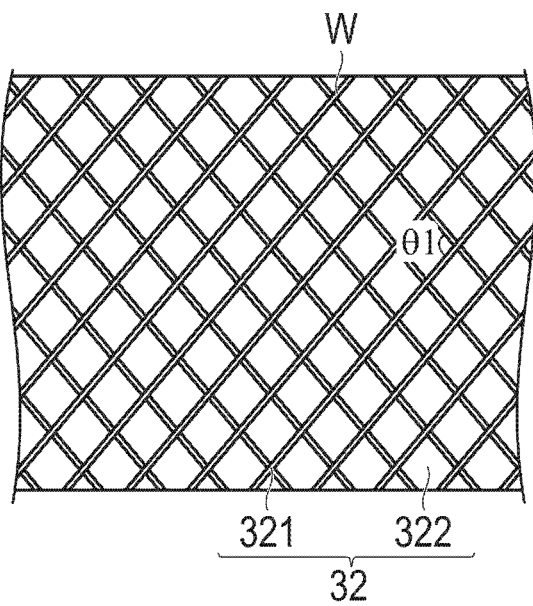
FIG. 5 is a view for describing a braiding angle of a first reinforcing member.

The enlarged portion 32 includes, as illustrated in FIG. 5, a first reinforcing member 321 including wires W braided to intersect one another and a first plastic layer 322 that covers the first reinforcing member 321.

Figure 6:
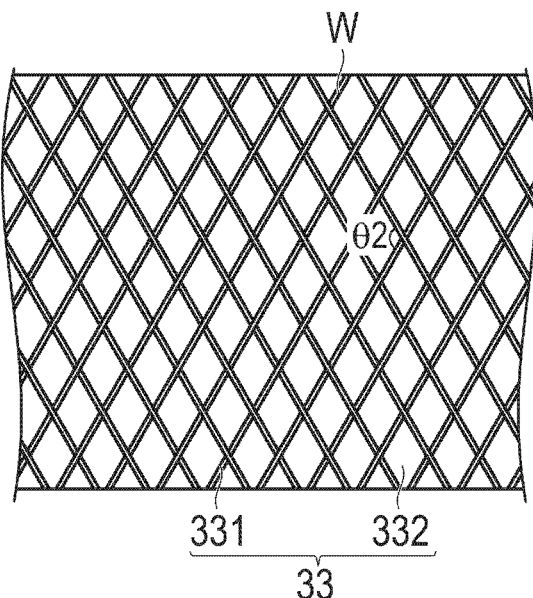
FIG. 6 is a view for describing a braiding angle of a second reinforcing member.

The shaft portion 33 includes, as illustrated in FIG. 6, a second reinforcing member 331 including wires W braided to intersect one another and a second plastic layer 332 that covers the second reinforcing member 331.

The first reinforcing member 321 is obtained by braiding wires W at a braiding angle θ1 as illustrated in FIG. 5. The second reinforcing member 331 is obtained by braiding wires W at a braiding angle θ2 as illustrated in FIG. 6.

Herein, as illustrated in FIGS. 5 and 6, the braiding angles θ1 and θ2 are defined as interior angles in the axial direction among angles formed by intersecting wires W.

The braiding angle θ1 of the first reinforcing member 321 is smaller than the braiding angle θ2 of the second reinforcing member 331 as illustrated in FIGS. 5 and 6. With this configuration, an inclination angle of the wires W included in the first reinforcing member 321 relative to the axial direction is smaller than an angle made when the braiding angle of the first reinforcing member 321 is larger than the braiding angle of the second reinforcing member 331. Note that the braiding angle θ1 of the first reinforcing member 321 may be larger than the braiding angle θ2 of the second reinforcing member 331.

Herein, along with the extension of the enlarged portion 32 in the axial direction, the wires W included in the first reinforcing member 321 of the enlarged portion 32 deforms in such a manner that the inclination angle relative to the axial direction becomes gradually small. When the inclination angle of the wires W included in the first reinforcing member 321 of the enlarged portion 32 relative to the axial direction reaches zero, the extension of the enlarged portion 32 in the axial direction is confined.

Accordingly, compared to a case where the braiding angle of the first reinforcing member 321 is larger than the braiding angle of the second reinforcing member 331, making the braiding angle θ1 of the first reinforcing member 321 smaller than the braiding angle θ2 of the second reinforcing member 331 decreases an extension length of the enlarged portion 32 in the axial direction when inserting the stylet 50 into the catheter 30.

The braiding angle θ1 of the first reinforcing member 321 is, but not particularly limited to, 100 degrees to 120 degrees. Furthermore, the braiding angle θ2 of the second reinforcing member 331 is, but not particularly limited to, 130 degrees to 150 degrees. In this manner, making the braiding angle θ2 of the second reinforcing member 331 larger than the braiding angle θ1 of the first reinforcing member 321 enhances the anti-kinking properties of the second reinforcing member 331. Therefore, it is possible to preferably insert the catheter 30 into the femoral vein having a complicated structure of a living body.

The first reinforcing member 321 of the enlarged portion 32 is braided more loosely than the second reinforcing member 331 of the shaft portion 33 as illustrated in FIGS. 5 and 6. With this configuration, it is possible to make the enlarged portion 32 softer and higher in elasticity than the shaft portion 33.

The wires W in this embodiment include a known shape-memory material such as shape-memory metal and shape-memory resin. Examples of the shape-memory metal include titanium-based alloys (such as Ni—Ti, Ti—Pd, and Ti—Nb—Sn) and copper-based alloys. Examples of the shape-memory resin include acrylic resin, trans-isoprene polymer, polynorbornene, styrene-butadiene copolymer, and polyurethane.

Since the wires W include a shape memory material, a contraction length of the enlarged portion 32 in the axial direction when removing the catheter 30 from the stylet 50 is equivalent to the extension length of the enlarged portion 32 in the axial direction when inserting the stylet 50 into the catheter 30.

Each wire W preferably has a diameter of 0.1 mm to 0.2 mm.

Setting the diameter of each wire W to 0.1 mm or more enables the wires W to preferably exercise a function as a reinforcing member that enhances the strength.

On the other hand, setting the diameter of each wire W to 0.2 mm or less makes it possible to design the enlarged portion 32 with a small outside diameter and a large inside diameter, thereby achieving both a reduction of the burden on a patient when inserting the catheter 30 into the body and a reduction of the pressure loss. In this embodiment, each wire W has a circular cross section, but the wires W are not limited thereto and may have a rectangular, square, or elliptical cross section.

The first plastic layer 322 of the enlarged portion 32 includes a soft material having a lower degree of stiffness than a material used in the second plastic layer 332 of the shaft portion 33. With this configuration, it is possible to make the enlarged portion 32 softer and higher in elasticity than the shaft portion 33.

The first and second plastic layers 322 and 332 are formed using, for example, vinyl chloride, silicon, polyethylene, nylon, urethane, polyurethane, fluororesin, thermoplastic elastomer resin, or a composite material of these examples.

Silicon materials are highly biocompatible and soft and hardly damage a blood vessel. Polyethylene materials are soft and yet stiff enough to withstand pressure. Polyethylene materials also have biocompatibility comparable to silicon materials. Polyethylene materials are stiffer than silicon and easier to insert into a thin blood vessel. Furthermore, polyurethane materials have a feature of becoming soft after insertion. The first and second plastic layers 322 and 332 may employ an appropriate material, considering the features of these materials.

Alternatively, a hydrophilic coating may be applied to a polyurethane material. A tube using such a material has a smooth surface, facilitates insertion into a blood vessel, and hardly damages the wall of a blood vessel. Blood and proteins are less likely to adhere to the surface, which offers the prospect of preventing thrombus formation.

A method for forming the enlarged portion 32 and the shaft portion 33 is not particularly limited and may employ dip coating (immersion) or insert molding. At least the outer surfaces of the reinforcing members 321 and 331 may be covered with the plastic layers 322 and 332.

The enlarged portion 32 includes, as illustrated in FIG. 2, the second side hole 46. In FIG. 2, the enlarged portion 32 includes a plurality of second side holes 46 (four holes in FIG. 2) in the axial direction. The plurality of second side holes 46 is preferably arranged in the circumferential direction. The second side holes 46 function as blood removal holes.

The shaft portion 33 includes, as illustrated in FIG. 2, the first side hole 63. The first side hole 63 functions as a blood removal hole. It is preferable that a plurality of first side holes 63 is arranged in the circumferential direction. In this embodiment, the shaft portion 33 includes four first side holes 63 in the circumferential direction. With this configuration, even when one first side hole 63 sticks to a blood vessel wall and the hole is closed, blood is removed from other first side holes 63 that are not closed, which enables stable blood circulation.

The distal tip 41 is disposed in the distal end of the enlarged portion 32 as illustrated in FIGS. 2 to 4. The distal tip 41 has a shape having a tapered outside diameter which is gradually decreasing moving toward the distal side.

The inside of the distal tip 41 is provided with a flat receiving surface 48 that abuts against a flat surface 51D of the stylet 50 which is used prior to the insertion of the catheter 30 into a living body.

The distal tip 41 is configured, as illustrated in FIG. 3, to house distal ends of the wires W. The distal tip 41 includes the through-hole 47. The through-hole 47 functions as a blood removal hole. The through-hole 47 of the distal tip 41 is a part of the lumen 30A of the catheter 30. The distal tip 41 is formed from, for example, urethane.

The clamping tube 34 is disposed in the proximal side of the shaft portion 33 as illustrated in FIGS. 2 to 4. The inside of the clamping tube 34 is provided with a lumen through which the stylet 50 is inserted. The clamping tube 34 is formed using a material similar to one used in the catheter tube 31.

The catheter connector 35 connects the shaft portion 33 and the clamping tube 34 as illustrated in FIGS. 2 and 4. The inside of the catheter connector 35 is provided with a lumen through which the stylet 50 is inserted.

As illustrated in FIGS. 2 to 4, the lock connector 36 is connected to the proximal side of the clamping tube 34. The inside of the lock connector 36 is provided with a lumen through which the stylet 50 is inserted. The proximal side of the lock connector 36 has the outer surface including a male screw 36A provided with a thread.

Figure 7:
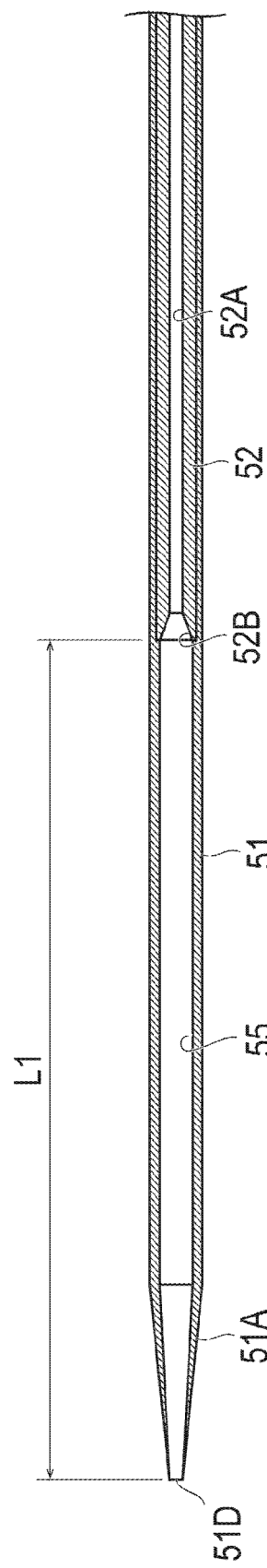
FIG. 7 is a schematic cross-sectional view illustrating a configuration of the stylet according to the embodiment.
Figure 8:
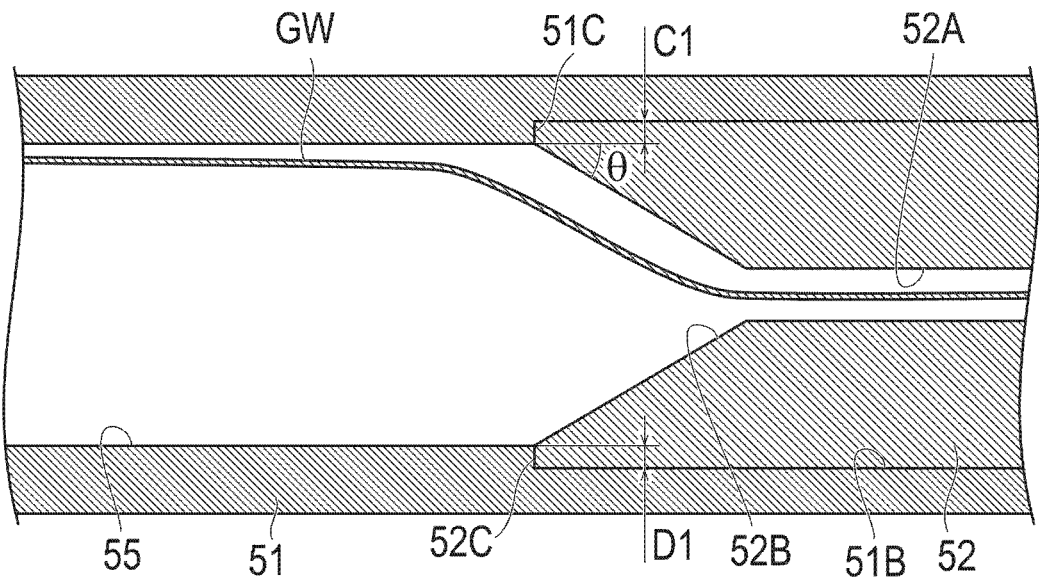
FIG. 8 is a partially enlarged view of part A in FIG. 7.
Figure 9:
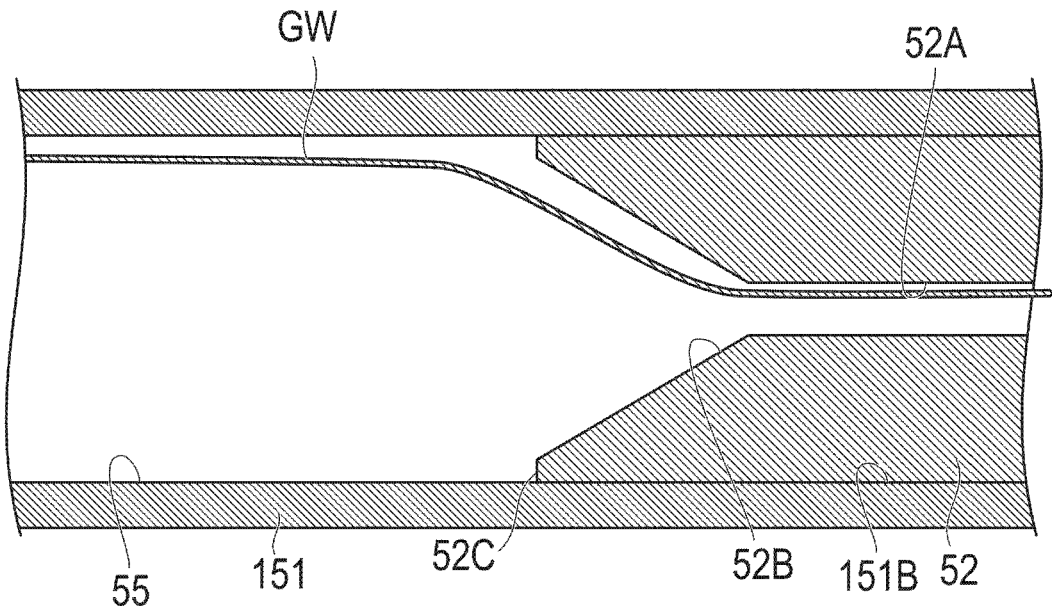
FIG. 9 is a view corresponding to FIG. 8 except that an outer layer tube is not provided with a recess.

Next, with reference to FIGS. 7 to 10, a configuration of the stylet 50 according to this embodiment will be described. FIGS. 7 and 8 are schematic cross-sectional views illustrating the configuration of the stylet 50 according to this embodiment. FIG. 9 is a view corresponding to FIG. 8 except that the outer layer tube is not provided with a recess.

Figure 10:
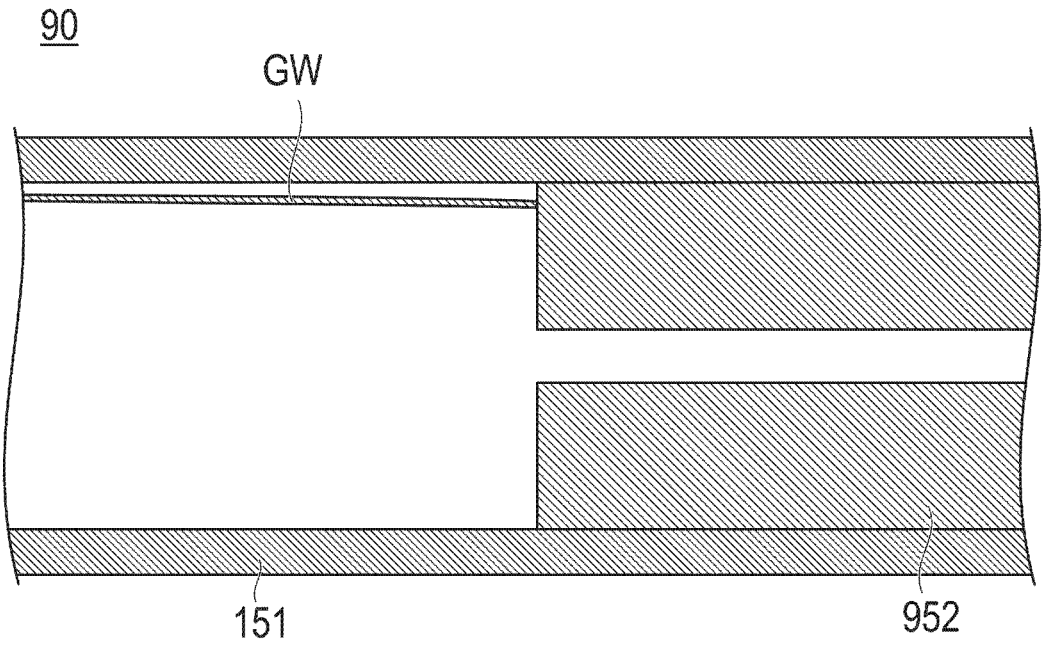
FIG. 10 is a view corresponding to FIG. 8 except that the stylet is not provided with a reduced diameter portion nor a recess of the outer layer tube.

FIG. 10 is a view corresponding to FIG. 8 except that the stylet is not provided with a reduced diameter portion nor a recess of the outer layer tube.

As illustrated in FIGS. 7 and 8, the stylet 50 includes an outer layer tube 51 extending in the axial direction and an inner layer tube 52 disposed in the inner periphery of the outer layer tube 51.

The outer layer tube 51 is configured to have an outside diameter equal to the inside diameter of the shaft portion 33. The expression "equal to the inside diameter of the shaft portion 33" indicates not only "completely identical" but also "identical within an acceptable margin of error". The outer layer tube 51 includes a lumen 55 where the inner layer tube 52 is disposed.

A distal portion 51A of the outer layer tube 51 is tapered, as illustrated in FIG. 7, having a diameter gradually reduced moving toward the distal end. With this configuration, since the outer periphery of the distal portion 51A of the outer layer tube 51 has a gently tapered shape, when the stylet 50 is inserted into the catheter 30 and combined, the catheter 30 conforms with the shape of the distal portion 51A and is tapered. Accordingly, the catheter 30 is enhanced in insertability into a living body.

The outer layer tube 51 has an inner peripheral surface provided with a recess 51B that is recessed radially outward as illustrated in FIGS. 7 and 8, wherein recess 51B extends axially only along an axial portion of outer layer tube 51 at the proximal side. The recess 51B of the outer layer tube 51 is configured to have an inside diameter slightly larger than an outside diameter of the inner layer tube 52. The inner layer tube 52 is fixed to the outer layer tube 51 while a distal portion 52C of a reduced thickness portion 52B (resulting from a gradually increasing inner diameter moving toward the distal end) in the inner layer tube 52 abuts against a distal portion 51C of the recess 51B in the outer layer tube 51.

The outer layer tube 51 has a distal end including the flat surface 51D that abuts against the receiving surface 48 of the distal tip 41 as illustrated in FIG. 2

The outer layer tube 51 has an entire axial length longer than that of the catheter 30 before the enlarged portion 32 is extended. The entire axial length of the outer layer tube 51 is configured to be equal to that of the catheter 30 after the enlarged portion 32 is extended.

The outer layer tube 51 has an outside diameter of 4.0 to 9.0 mm but is not particularly limited thereto. The outer layer tube 51 has an inside diameter of 1.2 to 7.0 mm but is not particularly limited thereto. The recess 51B formed in the inner periphery of the outer layer tube 51 has a depth C1 of 0.9 to 3.4 mm but is not particularly limited thereto. In addition, a length Li from the distal portion 51C of the recess 51B in the outer layer tube 51 to the flat surface 51D of the outer layer tube 51 (see FIG. 7) is, but not particularly limited to, 50 to 150 mm.

The outer layer tube 51 has an elongated body having relatively high rigidity. A material included in the outer layer tube 51 is not particularly limited and may be similar to the materials of the first and second plastic layers 322 and 332.

The inner layer tube 52 is disposed in the inner periphery of the outer layer tube 51.

The inner layer tube 52 includes a lumen 52A that allows insertion of a guidewire GW as illustrated in FIG. 8. The outer layer tube 51 and the inner layer tube 52 are guided by the guidewire GW and inserted into a living body together with the catheter 30.

The inner layer tube 52 is configured to have an outside diameter uniform in the axial direction.

In the inner layer tube 52, the distal portion 52C has the inner periphery provided with the reduced diameter portion 52B having a tapering diameter which is gradually reduced moving from distal portion 52C toward the proximal side as illustrated in FIGS. 7 and 8. In this embodiment, the tapered diameter portion 52B has a linear shape (a linear taper) as illustrated in FIG. 8. The tapered diameter portion 52B preferably has a taper angle θ of 80 degrees or less but is not particularly limited thereto. With a taper angle of 80 degrees or less, when the catheter assembly 7 is inserted into a living body along the guidewire GW, the guidewire GW is guided into the lumen 52A of the inner layer tube 52 along the reduced diameter portion 52B and passes through the lumen 52A of the inner layer tube 52.

The distal portion 52C of the tapered diameter portion 52B has a predetermined wall thickness Dl as illustrated in FIG. 8. It is preferable that the wall thickness Dl is substantially equal to the depth C1 of the recess 51B formed in the inner periphery of the outer layer tube 51 as illustrated in FIG. 8. With this configuration, no step is formed in the distal portion 52C of the inner layer tube 52, which enables the guidewire GW to pass through the lumen 52A of the inner layer tube 52 along the reduced diameter portion 52B when inserting the catheter assembly 7 into a living body along the guidewire GW. Even when the depth C1 is larger than the wall thickness Dl, the above effect is achieved.

As illustrated in FIG. 9, for example, in a case where the recess 51B is not disposed in an outer layer tube 151, there is formed a step corresponding to the wall thickness Dl of the distal portion 52C of the reduced diameter portion 52B. For this reason, when the catheter assembly 7 is inserted into a living body along the guidewire GW, the guidewire GW comes into contact with the distal portion 52C of the reduced diameter portion 52B, which may impede preferable insertion of the catheter assembly 7. In contrast, the stylet 50 according to this embodiment has the outer layer tube 51 provided with the recess 51B as illustrated in FIG. 8 and enables preferable insertion of the catheter assembly 7. Note that the configuration without the recess 51B in the outer layer tube 151 is included in the invention since such a configuration prevents the guidewire GW from bumping into the inner layer tube 52 as compared with the following configuration without the reduced diameter portion 52B.

As Comparative Example, FIG. 10 discloses a catheter assembly 90 having an inner layer tube 952 without the reduced diameter portion 52B and the outer layer tube 151 without the recess 51B. Without the reduced diameter portion 52B, as in the catheter assembly 90 according to Comparative Example, a step corresponding to a thickness of the inner layer tube 952 is formed. For this reason, when the catheter assembly 90 is inserted into a living body along the guidewire GW, the guidewire GW comes into contact with the inner layer tube 952, which would make it difficult to insert the catheter assembly 90.

The inner layer tube 52 has an outside diameter of 1.3 to 7.0 mm but is not particularly limited thereto. The inner layer tube 52 has an inside diameter of 1.1 to 5.0 mm but is not particularly limited thereto.

The inner layer tube 52 has an elongated body having relatively high rigidity. The inner layer tube 52 includes a material stiffer than that of the outer layer tube 51. A material included in the inner layer tube 52 is not particularly limited and may be similar to the materials of the first and second plastic layers 322 and 332. With this configuration, it is possible to make the distal end of the stylet 50 relatively flexible while ensuring high rigidity of the stylet 50 at the proximal end. Accordingly, the stylet 50 prevents body tissues from being damaged when the catheter assembly 7 is inserted into a living body, and at the same time, the stylet 50 has resilience that enables transmission of a pushing force toward the distal side caused by a hand operation to the distal tip 41.

The stylet 50 also includes, as illustrated in FIG. 2, a stylet hub 53 to which the proximal ends of the outer layer tube 51 and the inner layer tube 52 are fixed and a screw ring 54 disposed in the distal end of the stylet hub 53.

The stylet hub 53 disposed in the proximal ends of the outer layer tube 51 and the inner layer tube 52 is graspable. After the catheter 30 is retained in the living body, the stylet hub 53 is pulled toward the proximal side, whereby the stylet 50 is removed from the catheter 30.

The screw ring 54 includes a lumen having the inner surface including a female screw (not illustrated) provided with a thread groove. When the female screw of the screw ring 54 is screwed in the male screw 36A of the lock connector 36, the stylet 50 is attached to the catheter 30.

<Usage of Stylet>

Hereinafter described is how to use the stylet 50.

First, the inner layer tube 52 is fixed to the outer layer tube 51 to prepare the stylet 50. The stylet 50 is inserted into the lumen 30A of the catheter 30. The stylet 50 passes through the shaft portion 33 and the enlarged portion 32 in order, and the flat surface 51D of the outer layer tube 51 of the stylet 50 abuts against the receiving surface 48 of the distal tip 41.

As illustrated in FIG. 2, the outer layer tube 51 has an entire axial length longer than that of the catheter 30 before the enlarged portion 32 is extended. For this reason, while the flat surface 51D of the outer layer tube 51 of the stylet 50 abuts against the receiving surface 48 of the distal tip 41, the enlarged portion 32 is pressured toward the distal side.

The distal end of the enlarged portion 32 is pulled toward the distal side. Accordingly, the catheter 30 receives an axial extension force, and the enlarged portion 32 which has relatively high elasticity in the catheter 30 stretches in the axial direction.

The female screw of the screw ring 54 is then screwed in the male screw 36A disposed in the lock connector 36 of the catheter 30, whereby the stylet 50 is attached to the catheter 30.

Next, the catheter 30 into which the stylet 50 is inserted is inserted along the guidewire GW which is inserted in advance into a target site in a living body. In the stylet 50 according to this embodiment, since the inner layer tube 52 includes the reduced diameter portion 52B and the outer layer tube 51 is provided with the recess 51B, it is possible to preferably insert the catheter assembly 7 along the guidewire GW. Since the stylet 50 is inserted into the catheter 30, the enlarged portion 32 has an outside diameter substantially equal to that of the shaft portion 33, and it is possible to insert the catheter 30 into the living body in a minimally invasive manner, which reduces the burden on the body of a patient.

The catheter 30 is inserted into the living body until the through-hole 47 of the distal tip 41 and the second side hole 46 of the catheter tube 31 reach the right atrium and the first side hole 63 of the catheter tube 31 reaches the inferior vena cava, whereby the catheter 30 is retained. While the through-hole 47, first side hole 63, and second side hole 46 are placed in the objects of blood removal, the enlarged portion 32 is placed in the inferior vena cava, a relatively large blood vessel, and the shaft portion 33 is placed in the femoral vein, a relatively small blood vessel.

Next, the stylet 50 and the guidewire GW are retracted from the catheter 30. The stylet 50 and the guidewire GW are temporarily pulled to the position of the clamping tube 34 of the catheter 30, and after the clamping tube 34 is clamped by a pair of forceps (not illustrated), the stylet 50 and the guidewire GW are completely retracted from the catheter 30. Removing the stylet 50 from the lumen 30A of the catheter 30, the catheter 30 is free from the axial extension force applied to the catheter 30 from the stylet 50. Accordingly, the enlarged portion 32 shrinks in the axial direction and the enlarged portion 32 increases in inside diameter. Therefore, it is possible to reduce the pressure loss inside the enlarged portion 32 and it is possible to ensure a desired amount of fluid flow.

Next, the lock connector 36 of the catheter 30 is connected to the blood removal tube 11 of the extracorporeal circulation device in FIG. 1. After confirming that the connection of the catheter for blood supply is completed, the pair of forceps of the clamping tube 34 is released to start extracorporeal circulation.

On completion of the extracorporeal circulation, the catheter 30 is retracted from the blood vessel, and the insertion site is repaired by surgical hemostasis as necessary.

As described above, the stylet 50 according to this embodiment is configured to be insertable into the catheter 30 including the lumen 30A that allows passage of blood. The stylet 50 includes the outer layer tube 51 extending in the axial direction and the inner layer tube 52 disposed in the inner periphery of the outer layer tube 51, having a hollow shape, and formed from a material stiffer than that of the outer layer tube 51. In the inner layer tube 52, the distal portion has the inner periphery provided with the reduced diameter portion 52B having a diameter reduced toward the proximal side in the axial direction. According to the stylet 50 including the outer layer tube 51 extending in the axial direction and the inner layer tube 52 disposed in the inner periphery of the outer layer tube 51 and formed from a material stiffer than that of the outer layer tube 51, it is possible to ensure flexibility in the distal side and a desired degree of stiffness in the proximal side while preventing a kink or breakage. In addition, since the inner layer tube 52 has the reduced diameter portion 52B, when the catheter assembly 7 is inserted into a living body along the guidewire GW, it is possible to pass the guidewire GW through the lumen 52A of the inner layer tube 52 along the reduced diameter portion 52B. In this manner, it is possible to provide the stylet 50 that ensures flexibility in the distal side and stiffness in the proximal side and enables preferable insertion of the catheter assembly 7 along the guidewire GW while preventing a kink or breakage.

Furthermore, according to the stylet 50 having the above configuration, appropriately changing the axial position of the distal end of the inner layer tube 52 relative to the outer layer tube 51 makes it possible to appropriately control the range where the distal end of the stylet 50 exerts flexibility.

Moreover, the outer layer tube 51 has the inner periphery provided with the recess 51B that is recessed radially outward, and the inner layer tube 52 is fixed to the outer layer tube 51 while the distal portion 52C of the inner layer tube 52 abuts against the distal portion 51C of the recess 51B of the outer layer tube 51. According to the stylet 50 with this configuration, it is possible to insert the catheter assembly 7 more preferably along the guidewire GW.

Still further, the reduced diameter portion 52B has a linear tapered shape. According to the stylet 50 with this configuration, it is possible to form the reduced diameter portion 52B with ease.

<Modification of Catheter>

Figure 11:
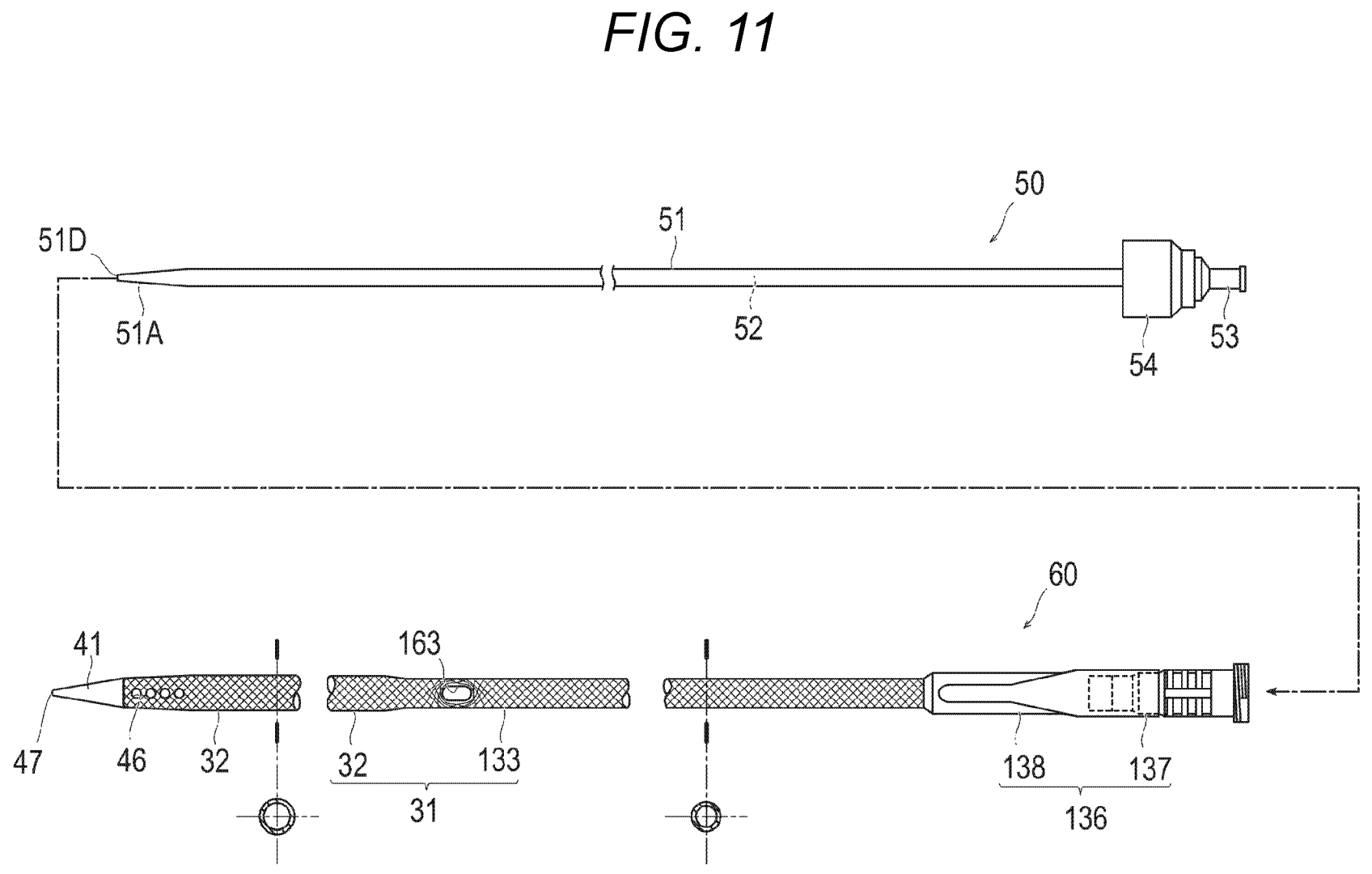
Figure 12:
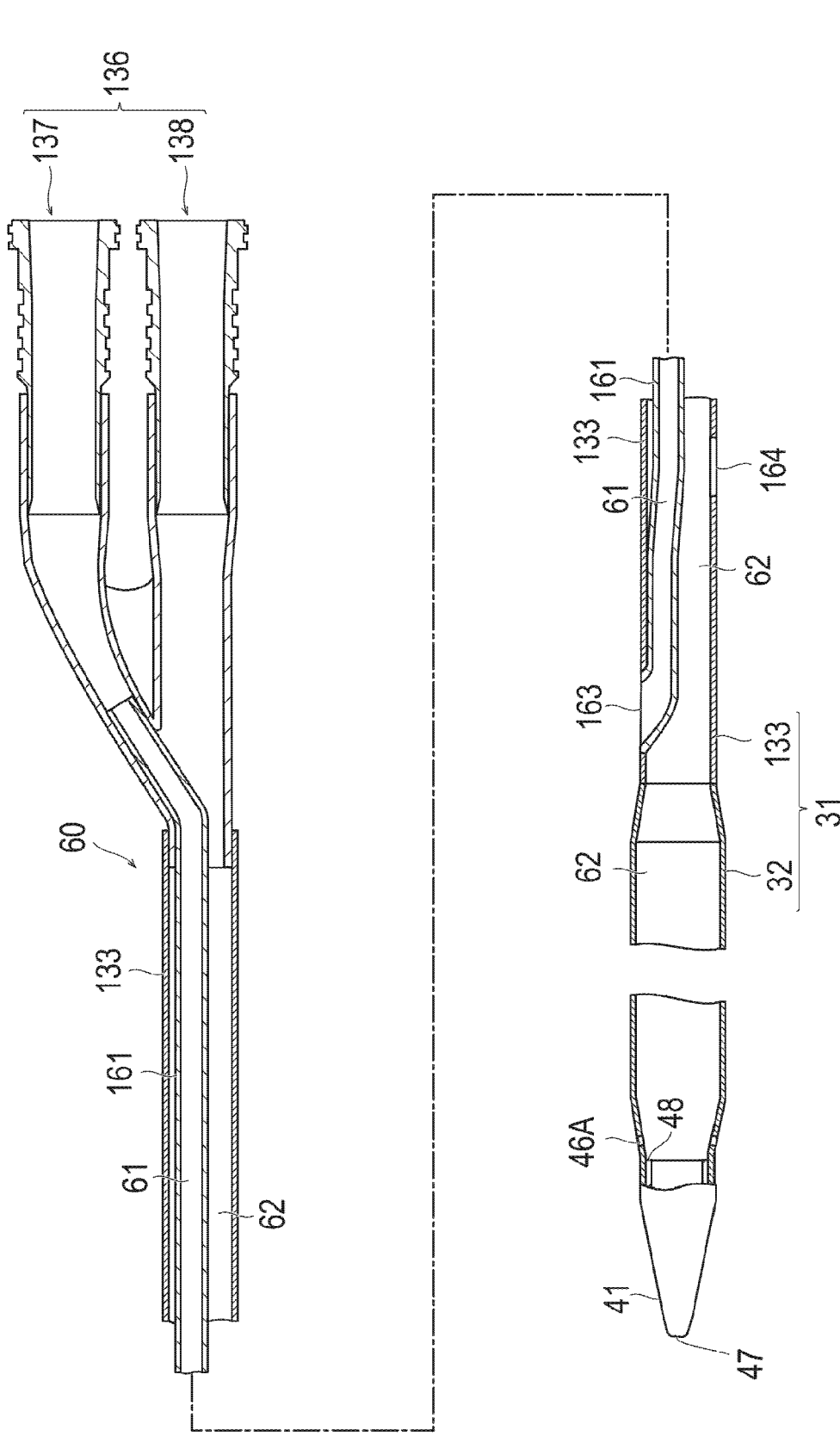
FIG. 12 is a cross-sectional side view of the double lumen catheter.
Figure 13:
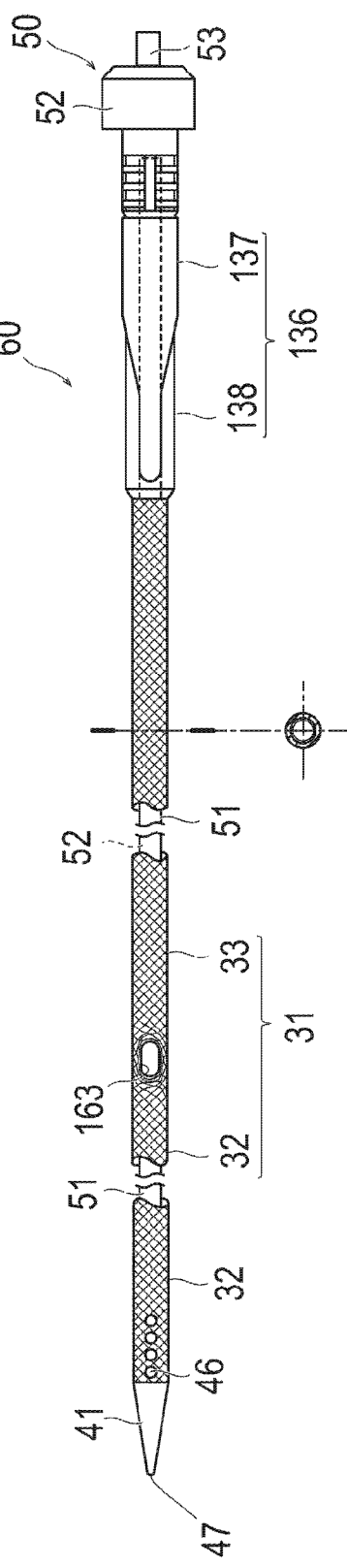
FIG. 13 is a plan view illustrating the double lumen catheter after the stylet according to the embodiment is inserted thereinto.

Next, a modification of the catheter will be described. In the embodiment, the stylet 50 is applied to the catheter 30 including one lumen 30A. However, the stylet 50 is applicable to a catheter 60 provided with a double lumen as illustrated in FIGS. 11 to 13. With reference to FIGS. 11 to 13, hereinafter described is a configuration of the catheter 60 including a double lumen.

The catheter 60 is what is called a double lumen catheter that can perform blood supply and blood removal simultaneously. Therefore, in this embodiment, surgery is performed with one catheter 60 instead of two catheters, that is, the venous catheter (catheter for blood removal) 5 and the arterial catheter (catheter for blood supply) 6 used in the extracorporeal circulation device of FIG. 1.

As illustrated in FIGS. 11 and 12, in the catheter 60, a third tube 161 including a first lumen 61 communicating with a side hole for blood supply 163 has a double tube structure disposed in a lumen of a shaft portion 133.

According to the catheter 60, it is possible to perform extracorporeal circulation using a Veno-Venous (VV) oxygenator. In this extracorporeal circulation, a pump of an extracorporeal circulation device is actuated to remove blood from a vein (vena cava) of a patient, and the oxygenator exchanges gases in the blood to oxygenate the blood, thereby returning the blood to the vein (vena cava) of the patient.

The catheter 60 includes, as illustrated in FIGS. 11 to 13, an enlarged portion 32, the shaft portion 133, a distal tip 41 disposed in a distal end of the enlarged portion 32, and the third tube 161 disposed in the lumen of the shaft portion 133. The enlarged portion 32 and the distal tip 41 are similar to those included in the catheter 30 of the first embodiment, and the details will be omitted.

As illustrated in FIG. 12, the catheter 60 includes the first lumen 61 functioning as a blood supply channel and a second lumen 62 functioning as a blood removal channel.

The first lumen 61 is formed in a lumen of the third tube 161. The second lumen 62 is formed in the enlarged portion 32 and the lumen of the shaft portion 133, penetrating these members from the distal end to the proximal end.

The shaft portion 133 is provided with the side hole for blood supply 163 which communicates with the first lumen 61 serving as the blood supply channel.

The shaft portion 133 is provided with a side hole for blood removal 164 which communicates with the second lumen 62 serving as the blood removal channel.

The side hole for blood supply 163 and the side hole for blood removal 164 have an elliptical shape.

The third tube 161 is inserted into the second lumen 62 from the proximal side of the shaft portion 133 and linked to the side hole for blood supply 163.

The side hole for blood supply 163 is placed in an object of blood supply within a living body, and blood oxygenated by the oxygenator is supplied to the living body through the side hole for blood supply 163.

A through-hole 47 included in the distal tip 41, a second side hole 46 included in the enlarged portion 32, and the side hole for blood removal 164 included in the shaft portion 133 are placed in different objects of blood removal in a living body and are configured to remove blood efficiently. Furthermore, even when one of the through-hole 47, second side hole 46, and side hole for blood removal 164 sticks to a blood vessel wall and the hole is closed, blood is removed from other holes that are not closed, which enables stable extracorporeal circulation.

In this embodiment, the catheter 60 is inserted from the internal jugular vein in the neck and a distal end of the catheter 60 is retained in the inferior vena cava through the superior vena cava and the right atrium. The right atrium is an object of blood supply, and the superior vena cava and the inferior vena cava are both objects of blood removal.

While the stylet 50 is inserted into the catheter 60 as illustrated in FIG. 13, the catheter 60 is inserted into the living body in such a manner that the through-hole 47 of the distal tip 41 and the second side hole 46 of the enlarged portion 32 are placed in the inferior vena cava and the side hole for blood removal 164 of the shaft portion 133 is placed in the internal jugular vein, whereby the catheter 60 is retained.

The enlarged portion 32 is configured to be larger than the shaft portion 133 in inside diameter. While the through-hole 47, second side hole 46, and side hole for blood removal 164 are placed in the objects of blood removal, the enlarged portion 32 is placed in the inferior vena cava, a relatively large blood vessel, and the shaft portion 133 is placed in the femoral vein, a relatively small blood vessel.

As illustrated in FIG. 12, a lock connector 136 includes a first lock connector 137 communicating with the first lumen 61 and a second lock connector 138 disposed in parallel with the first lock connector 137 and communicating with the second lumen 62. The lock connector 136 is a Y-shaped Y connector formed by branching the first lock connector 137 from the second lock connector 138.

The first lock connector 137 is coupled to a proximal portion of the third tube 161. The second lock connector 138 is coaxially coupled to a proximal portion of the shaft portion 133. A blood supply tube (blood supply line) is connected to the first lock connector 137, and a blood removal tube (blood removal line) is connected to the second lock connector 138.

In this manner, according to the catheter 60 of this embodiment, one catheter plays a role in both removing and supplying of blood.

<Modification of Catheter Assembly>

Next, a configuration of a catheter assembly 8 according to a modification will be described with reference to FIGS. 14 and 15. The aforementioned catheter assembly 7 according to the embodiment employs what is called an extension catheter in which the flat surface 51D of the outer layer tube 51 of the stylet 50 abuts against the receiving surface 48 of the distal tip 41 to extend the enlarged portion 32 of the catheter 30.

Figure 14:
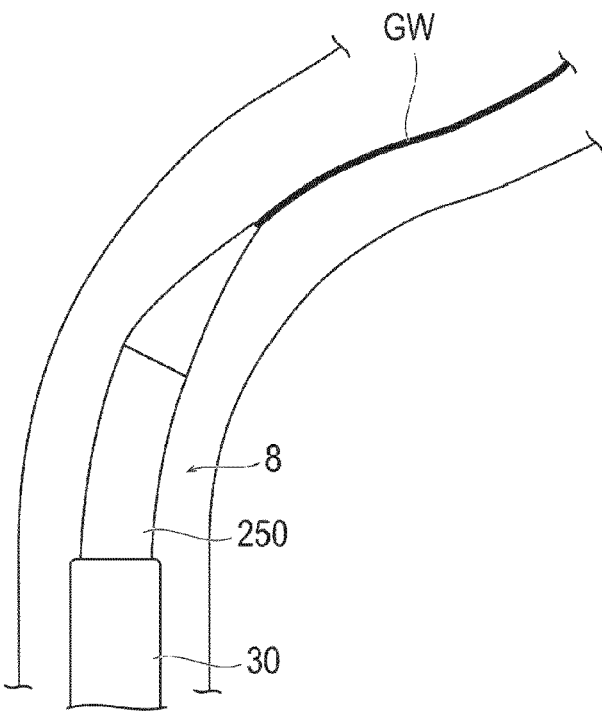
FIG. 14 is a schematic view of a catheter assembly according to a modification which is in use.

In contrast, in the catheter assembly 8 according to the modification, a stylet 250 as illustrated in FIG. 14 is protruded from a distal end of a catheter 30. In this configuration, a distal end of an outer layer tube 51 does not necessarily have a flat surface 51D and may have a shape without an edge.

Figure 15:
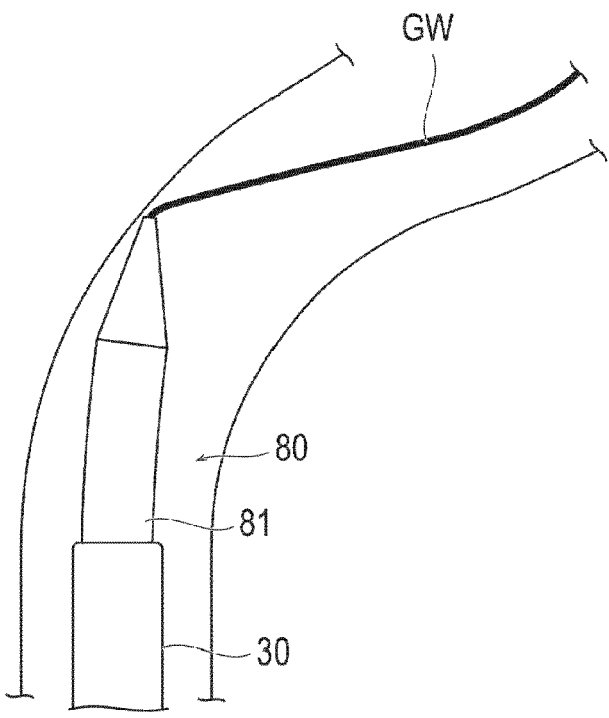
FIG. 15 is a schematic view of a catheter assembly according to a Comparative Example which is in use.

As illustrated in FIG. 15, for example, in a case where a stylet 81 is formed relatively stiff in a uniform manner along the axial direction, when a catheter assembly 80 is inserted along a guidewire GW, the stylet 81 has a bending problem and poor trackability along the guidewire GW and may unintentionally touch a blood vessel. In contrast, the catheter assembly 8 according to the modification employs the stylet 250 having flexibility in the distal side and a desired degree of stiffness in the proximal side, and the stylet 250 is easily bent as illustrated in FIG. 14 and has good trackability along the guidewire GW, thereby reducing the risk of damaging a blood vessel.

While the stylet 250 is inserted into the catheter 30, the distal end of the inner layer tube 52 is preferably disposed closer to the proximal side than the distal end of the catheter 30. This configuration enables an operator to hold the proximal side with high stiffness where the inner layer tube 52 is disposed, which facilitates the operation.

Although the catheter according to the invention has been described through the embodiments, the invention is not limited to the configurations described in the embodiments and modifications thereof and is appropriately changed based on the claims.

Figure 16:
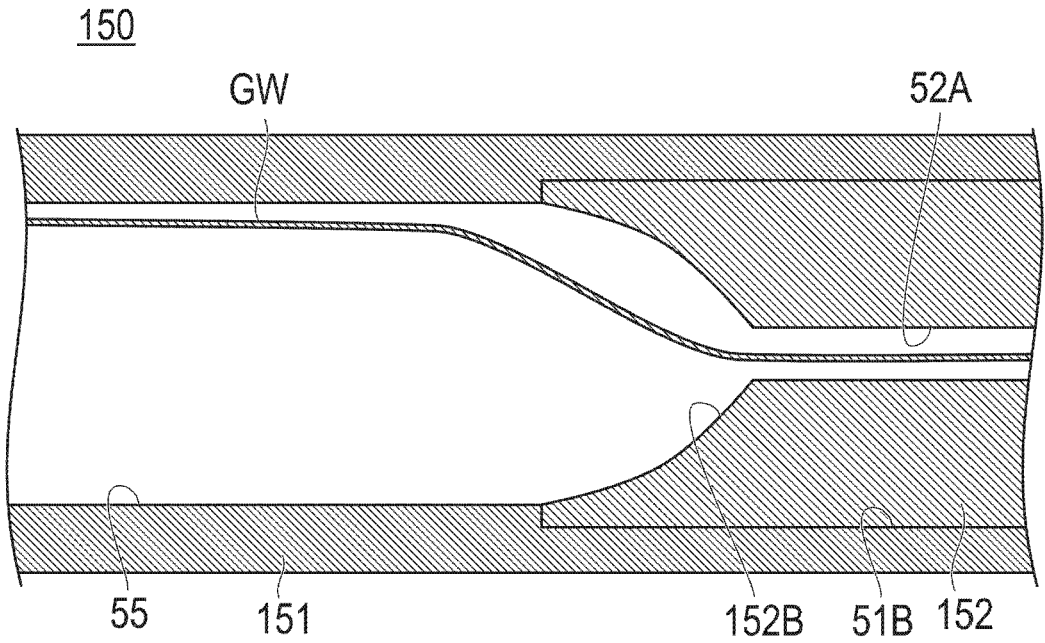
FIG. 16 is a view of a stylet according to a modification, corresponding to FIG. 8.

For example, in the above embodiment, the reduced diameter portion 52B has a linear shape. However, as illustrated in FIG. 16, a reduced diameter portion 152B may have a curved shape protruding toward the proximal side. According to a stylet 150 with this configuration, when a catheter assembly is inserted into a living body along a guidewire GW, the guidewire GW is preferably guided into a lumen 52A of an inner layer tube 152 along the curved shape of the reduced diameter portion 152B.

Furthermore, the material included in the wires W is not limited to a shape-memory material as long the material has a restoring force that enables it to return to its original shape and has a function of reinforcing a plastic layer, and the wires W may employ, for example, a known elastic material.

REFERENCE SIGNS LIST

7, 8 Catheter assembly
30, 60, 230 Catheter (percutaneous catheter)
30A Lumen of catheter
50, 150, 250 Stylet
51, 151 Outer layer tube
51B Recess
51C Distal portion of recess
52, 152 Inner layer tube
52B, 152B Reduced diameter portion
52C Distal portion of inner layer tube

What is claimed is:

1. A stylet configured to be insertable into a catheter including a lumen that allows passage of blood, the stylet comprising:
   a hollow outer layer tube extending in an axial direction between a distal end and a proximal end and having an inner periphery; and
   a hollow inner layer tube disposed in the inner periphery of the outer layer tube along an axial portion of the outer layer tube at the proximal end, and formed from a material stiffer than a material of the outer layer tube;
   the inner layer tube including a distal portion having a reduced thickness wherein an inner periphery of the inner layer tube is provided with a tapered diameter portion having an inner diameter which is gradually reduced from a distal tip toward a proximal side of the inner layer tube in the axial direction.

2. The stylet according to claim 1 wherein the inner periphery of the outer layer tube has a recess that is recessed radially outward within the axial portion of the outer layer tube at the proximal end; and
   wherein the inner layer tube is fixed to the outer layer tube within the recess with the distal portion of the inner layer tube abutting against a distal portion of the recess of the outer layer tube.

3. The stylet according to claim 1 wherein the tapered diameter portion has a linear shape.

4. The stylet according to claim 1 wherein the tapered diameter portion has a curved shape protruding toward the proximal side.

5. A catheter assembly comprising:
   a catheter including a lumen that allows passage of blood; and
   a stylet insertable into the lumen comprising:
      a hollow outer layer tube extending in an axial direction between a distal end and a proximal end and having an inner periphery; and
      a hollow inner layer tube disposed in the inner periphery of the outer layer tube along an axial portion of the outer layer tube at the proximal end, and formed from a material stiffer than a material of the outer layer tube;
      the inner layer tube including a distal portion having a reduced thickness wherein an inner periphery of the inner layer tube is provided with a tapered diameter portion having an inner diameter which is gradually reduced from a distal tip toward a proximal side of the inner layer tube in the axial direction.

6. The catheter assembly according to claim 5:
   wherein the inner periphery of the outer layer tube has a recess that is recessed radially outward within the axial portion of the outer layer tube at the proximal end; and
   wherein the inner layer tube is fixed to the outer layer tube within the recess with a distal end of the inner layer tube abutting against a distal portion of the recess of the outer layer tube;
   whereby the inner layer tube has the distal end disposed closer to the proximal end of the outer layer tube than the distal end of the outer layer tube.

7. The catheter assembly according to claim 5 wherein the tapered diameter portion has a linear shape.

8. The catheter assembly according to claim 5 wherein the tapered diameter portion has a curved shape protruding toward the proximal side.

9. A catheter assembly comprising:
   a catheter including a lumen that allows passage of blood; and
   a stylet insertable into the lumen for stretching the catheter, comprising:
      a hollow outer layer tube extending in an axial direction between a distal end and a proximal end and having an inner periphery, wherein the outer layer tube has a recess that is recessed radially outward within an axial portion of the outer layer tube at the proximal end; and
      a hollow inner layer tube disposed in the recess;
      wherein the inner layer tube is formed from a material which is stiffer than a material of which the outer layer tube is formed;
      whereby the stylet has a distal end which is relatively flexible compared to a proximal end of the stylet.

10. The catheter assembly according to claim 9 wherein the inner layer tube includes a distal portion having a reduced thickness wherein an inner periphery of the inner layer tube is provided with a tapered diameter portion having an inner diameter which is gradually reduced from a distal tip toward a proximal side of the inner layer tube in the axial direction.

11. The catheter assembly according to claim 10 wherein the tapered diameter portion has a linear shape.

12. The catheter assembly according to claim 10 wherein the tapered diameter portion has a curved shape protruding toward the proximal side.

* * * * *